(12) United States Patent
Naver et al.

(10) Patent No.: US 8,865,647 B2
(45) Date of Patent: Oct. 21, 2014

(54) PHARMACEUTICAL SOLUTION OF NON COVALENTLY BOUND ALBUMIN AND ACYLATED INSULIN

(75) Inventors: Helle Naver, Alleroed (DK); Svend Havelund, Bagsvaerd (DK); Peter Madsen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/505,188

(22) PCT Filed: Nov. 1, 2010

(86) PCT No.: PCT/EP2010/066553
§ 371 (c)(1),
(2), (4) Date: Jun. 11, 2012

(87) PCT Pub. No.: WO2011/051486
PCT Pub. Date: May 5, 2011

(65) Prior Publication Data
US 2012/0245085 A1  Sep. 27, 2012

Related U.S. Application Data

(60) Provisional application No. 61/259,659, filed on Nov. 10, 2009, provisional application No. 61/381,760, filed on Sep. 10, 2010.

(30) Foreign Application Priority Data

Nov. 2, 2009 (EP) ..................... 09174762
Aug. 23, 2010 (EP) ..................... 10173750

(51) Int. Cl.
*A61K 38/38* (2006.01)
*A61K 38/28* (2006.01)
*A61K 9/00* (2006.01)
*C07K 14/62* (2006.01)
*A61K 47/42* (2006.01)
*A61K 47/48* (2006.01)
*A61K 47/02* (2006.01)
*A61K 38/00* (2006.01)
*A61K 47/18* (2006.01)

(52) U.S. Cl.
CPC .............. *C07K 14/62* (2013.01); *A61K 9/0019* (2013.01); *A61K 47/42* (2013.01); *A61K 47/02* (2013.01); *A61K 47/48038* (2013.01); *A61K 38/00* (2013.01); *A61K 47/18* (2013.01); *A61K 47/48284* (2013.01)
USPC ............. 514/6.5; 514/1.1; 514/5.9; 514/15.2; 530/362; 530/363; 530/399

(58) Field of Classification Search
CPC ....... A61K 38/38; A61K 38/17; A61K 38/16; A61K 38/385; A61K 38/28; A61K 38/22; C07K 14/575; C07K 14/62; C07K 14/625; C07K 14/76; C07K 14/765
USPC ......................................... 514/6.5
See application file for complete search history.

(56) References Cited

U.S. PATENT DOCUMENTS

| | | | |
|---|---|---|---|
| 2,789,080 A * | 4/1957 | Christensen | .............. 514/6.4 |
| 4,492,684 A | 1/1985 | Goosen et al. | |
| 6,051,551 A | 4/2000 | Hughes et al. | |
| 2005/0222006 A1* | 10/2005 | Havelund et al. | ................ 514/3 |
| 2006/0019874 A1* | 1/2006 | Radhakrishnan et al. | ........ 514/3 |

FOREIGN PATENT DOCUMENTS

| | | | | |
|---|---|---|---|---|
| EP | 0911035 | * | 4/1999 | ............ A61K 38/28 |
| WO | WO 92/19260 | | 11/1992 | |
| WO | WO 2009/022005 | | 2/2009 | |

OTHER PUBLICATIONS

Markussen et al., Diabetologia (1996) 39: 281-288.*
Kurtzhals, P. et al., "Albumin Binding of Insiulins Acylated With Fatty Acids: Characterization of the Ligand-Protein Interaction and Correlation Between Binding Affinity and Timing of the Insulin Effect In Vivo", Biochemical Journal, 1995, vol. 312, No. 3, pp. 725-731.
Kurtzhals, P., "How to Achieve a Predictable Basal Insulin", Diabetes Metabolism, 2005, vol. 31, pp. 4S25-4S33.
Smith, R.M. et al., "Preparatio and Characterization of a Colloidal Gold-Insulin Complex With Binding and Biological Activities Identical to Native Insulin", The Journal of Histochemistry and Cytochemistry, 1988, vol. 36, No. 4, pp. 359-365.

* cited by examiner

*Primary Examiner* — Karlheinz R Skowronek
*Assistant Examiner* — Catherine Mader
(74) *Attorney, Agent, or Firm* — Rosemarie R. Wilk-Orescan

(57) ABSTRACT

If albumin is added to a pharmaceutical formulation containing acylated insulin described in WO 2009/022005 and WO 2009/022013, the acylated insulin can be kept in solution after subcutaneous injection.

11 Claims, 3 Drawing Sheets

PHARMACEUTICAL SOLUTION OF NON COVALENTLY BOUND ALBUMIN AND ACYLATED INSULIN

CROSS-REFERENCE TO RELATED APPLICATIONS

This application is a 35 U.S.C. §371 national stage application of International Patent Application PCT/EP2010/066553 (published as WO 2011/051486 A2), filed Nov. 1, 2010, which claimed priority of European Patent Application 09174762.6, filed Nov. 2, 2009 and European Patent Application 10173750.0, filed Aug. 23, 2010; this application further claims priority under 35 U.S.C. §119 of U.S. Provisional Application 61/259,659, filed Nov. 10, 2009 and U.S. Provisional Application 61/381,760, filed Sep. 10, 2010.

FIELD OF THIS INVENTION

The present invention relates to an injectable, pharmaceutical solution of an acylated insulin which, after subcutaneous injection, does not precipitate or precipitates only in an inferior or minor amount.

BACKGROUND OF THIS INVENTION

Diabetes mellitus is a metabolic disorder in which the ability to utilize glucose is partly or completely lost (designated diabetes 2 and diabetes 1, respectively). World vide, about 5% of all people suffer from diabetes and the disorder approaches epidemic proportions. Since the introduction of insulin in the early 1920's, continuous efforts have been made to improve the treatment of diabetes mellitus. Since many people suffering from diabetes are subject to chronic treatment over several decades, there is a major need for safe, convenient and life quality improving insulin formulations.

In the treatment of diabetes mellitus, many varieties of insulin formulations have been suggested and used, such as regular insulin, isophane insulin (designated NPH), insulin zinc suspensions (such as Semilente®, Lente®, and Ultralente®) and biphasic isophane insulin. Some of the commercial available insulin formulations are characterized by a fast onset of action and other formulations have a relatively slow onset but show a more or less prolonged action. Fast-acting insulin formulations are usually solutions of insulin, while retarded acting insulin formulations can be suspensions containing insulin in crystalline and/or amorphous form precipitated by addition of zinc salts alone or by addition of protamine or by a combination of both. Recently, also soluble prolonged acting insulin formulations have also been put on the market and in such formulations the insulin may be an acylated insulin.

Some previously invented insulins and insulin analogues which are acylated with a fatty acid chain with high affinity for albumin have—due to analogue design—high hydrophobicity or changed pI value (compared with that of human insulin). Subcutaneous injection of such an acylated insulin may result in precipitation by salting out or oligomer formation of the acylated insulin. Unfortunately, the precipitated, acylated insulin is only partly solubilised in the subcutis. One draw back of this is that these insulins when injected have limited bioavailability and, hence, it is difficult to control the administration of insulin.

It has turned out that it is extremely important for a diabetic patient to control the blood glucose level as much as possible. A good control of the blood glucose level will—in addition to the control of the diabetic disease—reduce the risk for complications such as cardiovascular diseases, amputation of legs and blindness.

In *J. Histochem. Cytochem.* 36 (1988), 359-65, receptor dynamics of gold-insulin complexes, stabilized with bovine serum albumin, was studied. No pharmaceutical formulations are mentioned therein.

The claims in U.S. Pat. No. 2,789,080 relates to an aqueous composition comprising insulin and an esterified animal albumin. Alternatively, the albumin can be amidificated. Since this patent claims priority from 1953, the insulin dealt with probably is porcine or bovine insulin.

Claim 1 in U.S. Pat. No. 4,492,684 relates to a composition comprising a matrix of partially cross-linked albumin and insulin, said cross-linking being achieved by the use of glutaraldehyde resulting in covalent bonds.

Claim 1 in U.S. Pat. No. 4,963,526 relates to a composition useful as an oral dosage form of insulin, said composition derived from a two phase liquid coacervate composition. According to claim 3 therein, said composition may, for example, contain albumin. Apparently, no acylated insulin is mentioned therein.

Claim 1 in U.S. Pat. No. 6,051,551 relates to a method of treating diabetes, comprising administering a fatty acid-acylated human insulin or insulin analogue by inhalation. According to columns 11 and 12 therein, formulations suitable for use with a sprayer or a nebulizer can also include an agent for stabilizing of the fatty acid-acylated insulin protein, such as, for example, a bulk protein. Bulk proteins include, for example, albumin. Albumin is not used in any of the working examples therein.

Claim 1 in WO 92/19260 relates to a peptide hormone solution said solution containing serum albumin in an amount capable of stabilizing the hormone to prevent precipitation thereof. In the only experimental example in said application, the hormone insulin, of an unknown species, is used.

Claim 20 in WO 02/064115 relates to a powder insulin formulation manufactured by lyophilization of a dispersion of a liquid insulin formulation according to claim 1 therein to which has been added a cryoprotectant which, for example, is albumin. No acylated insulins are mentioned therein.

Claim 1 in WO 2008/013938 relates to an aerosolizable formulation comprising an insulin derivative. At page 34 therein, albumin is mentioned as one of the many, possible ingredients in the aerosolizable formulation.

Claim 1 in WO 2008/034881 relates to novel, protease resistant insulin analogues which have been developed for oral administration for patients preferring that route of administration. The preparation of oral formulations is described therein at pages 31-34 and, at page 34, albumin is mentioned as one of the many, possible ingredients in the oral formulation.

OBJECTS OF THIS INVENTION

The object of this invention is to overcome or ameliorate at least one of the disadvantages of the prior art, or to provide a useful alternative.

Another aspect of this invention relates to the furnishing of a soluble, aqueous, pharmaceutical formulation which can be used to treat diabetes and which can be easily used to control or prevent diabetes.

Another aspect of this invention relates to the furnishing of a soluble, aqueous, pharmaceutical formulation containing an acylated insulin which, after subcutaneous injection, does not precipitate or precipitates only in an inferior or minor amount.

Another aspect of this invention relates to the furnishing of a soluble, aqueous, pharmaceutical formulation containing an acylated insulin which, after subcutaneous injection, does not oligomerise with albumin at the injection site to form an oligomer with a high molecular weigth, e.g., a molecular weigth of 440 kDa or oligomerises only in an inferior or minor amount.

Another aspect of this invention relates to the furnishing of a soluble, aqueous, pharmaceutical formulation containing an acylated insulin which has a more protracted pharmaceutical profile compared with the profile of the analogous formulation with a relatively higher content of albumin.

Another aspect of this invention relates to the furnishing of a formulation facilitating the regulating of the degree of protraction.

Another aspect of this invention relates to the furnishing of a formulation in which the degree of protraction can be more conveniently regulated that in a corresponding formulation not containing albumin.

Another aspect of this invention relates to the furnishing of an insulin formulation for which it is easier than for the known insulin preparations to foresee the degree of protraction.

Another aspect of this invention relates to the furnishing of an acylated insulin formulation for which it is easier than for the known insulin preparations to foresee the degree of protraction.

DEFINITIONS

Briefly, the term acylated insulin covers naturally occurring insulin and analogue thereof in which a moiety containing an acyl group has been attached to the amino group in a lysine residue. Usually such acyl groups originate from fatty acids, both mono and diacids, containing at least 16 carbon atoms and, preferably, containing not more than 38 carbon atoms, more preferred not more than 24 carbon atoms, more preferred not more than 22 carbon atoms, more preferred not more than 20 carbon atoms. Said moiety containing an acyl group may also contain other groups such as an alkylene glycol moiety. Preferably, the naturally occurring insulin or and analogue thereof which is acylated contains only a single lysine residue. Such a lysine residue can, for example, be attached to the A21 amino acid in which case the lysine residue is in the A22 position. Many acylated insulins have been described in the last decade and acylated insulins is a class of insulins which are known to the skilled art worker. A general formula of the acyl moiety connected to the insulin or analogue thereof is: $-X-OC-(-CH_2)_n-R$, wherein n is an integer in the range from 14 to 24, R is methyl or carboxy, $-(CH_2)_n-R$ is a straight chain, and X is a bond or a linker. In one embodiment, the term "acylated insulin" covers the acylated insulins described in WO 2009/022005 and WO 2009/022013 which are both incorporated by reference. Hence, acylated insulins are, for example, covered by claim 1 in each of these publications. Claim 1 in WO 2009/022005 reads as follows: "An acylated insulin analogue wherein the insulin analogue comprises a lysine residue connected C-terminally to the A21 amino acid residue or a peptide residue of up to 4 amino acid residues comprising a lysine residue which peptide residue is connected C-terminally to the A21 amino acid residue, characterized in that an acyl moiety comprising an alkylene glycol moiety is attached to the lysine residue in the A22 position or attached to a lysine residue present in the peptide residue that is attached to the C terminal end of the A21 amino acid residue and wherein there is only one lysine (K, Lys) in the insulin analogue." A more detailed explanation of said acylated insulins can be found in the two, last-mentioned PCT applications which are incorporated by reference. In one embodiment, the term "acylated insulin" covers the acylated insulins described in WO 2007/096431, for example in claim 1 in combination with claim 3. Hence, in this case, the term "acylated insulin" covers an insulin derivative comprising a parent insulin and a substituent, wherein the substituent is attached either to an ε-amino group of a Lys residue present in the A-chain of the parent insulin at position A8, A9, A10, A12, A14, A15, A17, A18, A21, A22, A23 or A24 or to an ε-amino group of a Lys residue in the B-chain of the parent insulin at position B1, B2, B3, B4, B20, B21 or B22, wherein the substituent comprises an acyl group having from 6 to 40 carbon atoms, and, preferably, the substituent has the general formula $CH_3-(CH_2)_n-CO-$, where n is an integer in the range from 4 to 38, and wherein the term "parent insulin" is an insulin analogue containing only one Lys residue in the A-chain and/or the B-chain. A more detailed explanation of said acylated insulins can be found in the last-mentioned PCT applications which is incorporated by reference. In another embodiment, the term "acylated insulin" covers the acylated insulins described in EP 1,991,576 B1, especially in claim 1 thereof and a more detailed explanation of said acylated insulins can be found in the last-mentioned EP patent which is incorporated by reference.

Herein, the term "analogues of naturally occurring insulins" and "insulin analogue" covers human insulin wherein one or more amino acid residues of the insulin have been substituted by other amino acid residues and/or wherein one or more amino acid residues have been deleted from the insulin and/or wherein one or more amino acid residues have been added and/or inserted to the insulin. The amino acids dealt with in this invention are, preferably, amino acids which can be coded for by a triplet ("codon") of nucleotides, vide genetic engineering. Herein, amino acids are, given by their common three letter codes, preferably: Gly, Pro, Ala, Val, Leu, Ile, Met, Cys, Phe, Tyr, Trp, His, Lys, Arg, Gln, Asn, Glu, Asp, Ser and Thr. In one embodiment, an insulin analogue comprises less than 8 modifications (substitutions, deletions, additions (including insertions) and any combination thereof) relative to the parent insulin, alternatively less than 7 modifications relative to the parent insulin, alternatively less than 6 modifications relative to the parent insulin, alternatively less than 5 modifications relative to the parent insulin, alternatively less than 4 modifications relative to the parent insulin, alternatively less than 3 modifications relative to the parent insulin, alternatively less than 2 modifications relative to the parent insulin.

Herein, the following abbreviations are used: "OEG" for 8-amino-3,6-dioxaoctanoic acid; "gGlu" (or "γGlu" or "y-Glu") for gamma-glutamic acid and "HSA" for human serum albumin. "Milli-Q" refers to water that has been purified and deionized to a high degree by a water purification systems manufactured by Millipore Corporation. The system monitors the ion concentration by measuring the electrical resistance of the water. Most Milli-Q systems dispense the water through a 0.22 μm membrane filter.

Herein, the term insulin dimeric constant is used for the insulin concentration where more than 90% of the insulin is in the dimeric form. Below this concentration an increasing amount of insulin is in the monomeric form.

SUMMARY OF THE INVENTION

Certain acylated insulins as described in the present invention have been found to precipitate in the subcutaneous tissue following subcutaneous injection of a soluble formulation with low ionic strength, for example, below 50 mM NaCl. Probably, precipitation is caused by the increase in ionic strength to 150 mM NaCl in the subcutis and is associated with low bioavailability.

It has, surprisingly, been found that addition of albumin, for example, serum albumin, to the insulin formulation (before it is administered) can prevent the acylated insulin formulations of the invention from precipitation following subcutaneous injection. Probably, the reason for the surprising effect obtained by the present invention it that the interaction between albumin and the acyl chain of acylated insulin in the solution intended for injection to a patient prevents the precipitation of the acylated insulin and restores the bioavailability of the acylated insulin after the injection has taken place (although this invention is not restricted to this being the reason for the observed inventive effect).

Furthermore, it has been found that the stoichiometry of albumin vs. acylated insulin in the formulation can be used to control the aggregation state of the insulin-albumin complex in the formulation, and thus, the degree of protraction following subcutaneous injection.

In one embodiment, this invention addresses acylated insulins which interact with albumin with a binding constant of at least 1 mM and, then, precipitate or aggregate after subcutaneous injection. Acylated insulins include, for example, insulins acylated in the A22K amino acid (A22K acylated insulins), as described herein.

DETAILED DESCRIPTION OF THIS INVENTION

Figure 1:
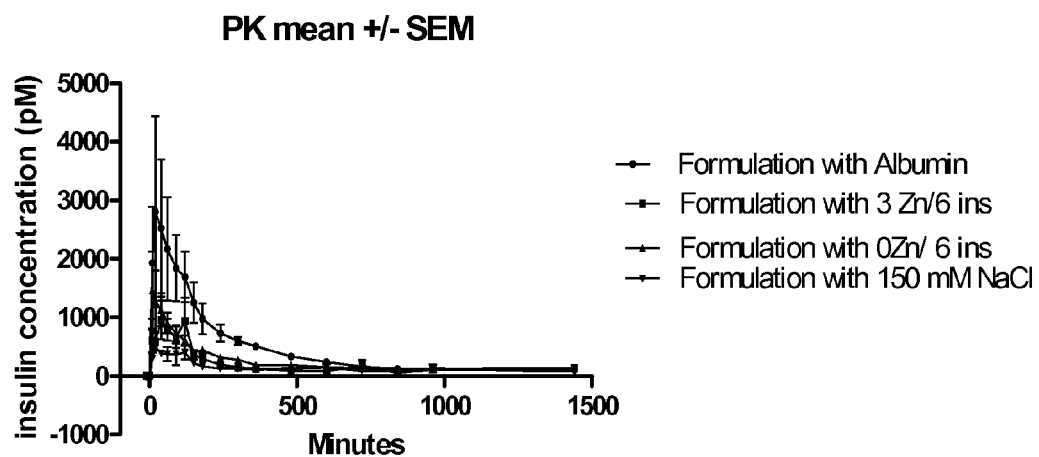
FIG. 1 is a graph showing the measured blood insulin concentration from time 0 to 1500 minutes after injection.

Briefly, this invention relates to formulations containing albumin and a salting out, acylated insulin wherein the albumin is not covalently bound to the salting out, acylated insulin. Salting out, acylated insulins can be divided into three sub groups of acylated insulins. Acylated insulins having a low solubility in a 150 mM NaCl solution containing three zinc ions per six insulin molecules, i.e. a solubility below 30%, as defined specifically in Test A below, are salting out, acylated insulins. Furthermore, also acylated insulins which form an insulin-albumin-oligomer with a molecular weight above 440,000, as defined specifically in Test B below, are salting out, acylated insulins. Furthermore, also acylated insulins having a low solubility in a 150 mM NaCl solution not containing zinc, i.e. a solubility below 50%, as defined specifically in Test C below, are salting out, acylated insulins.

It has been discovered that for certain acylated insulins, inter alia, acylated insulins having a low solubility in a 150 mM NaCl solution with or without zinc ions as defined herein, it is difficult to give a satisfactory prediction of the blood glucose profile in a patient after subcutaneous administration thereof. It is known that it is very important that the blood glucose profile does not vary very much during the day and night as, otherwise, this may give rise to late diabetic complications such as blindness, amputation of legs and other serious illnesses. It has now, surprisingly, been found that if such an acylated insulin formulation contains albumin, it is much easier to predict the patient's blood glucose profile.

Similarly, it has been discovered that for certain other acylated insulins, inter alia, acylated insulins which with albumin form an oligomer having a molecular weight above 440,000 as defined herein, it is also difficult to give a satisfactory prediction of the blood glucose profile in a patient after subcutaneous administration thereof. It has now, surprisingly, been found that if such an acylated insulin formulation contains albumin, it is much easier to predict the blood glucose profile.

The novel formulation of this invention is an aqueous, pharmaceutical solution containing albumin and an salting out acylated insulin wherein the albumin is not covalently bound to the salting out, acylated insulin which formulation is to be administered to the patient by injection.

If a formulation of an acylated insulin as defined herein not containing albumin is injected to a patient, precipitation of the acylated insulin may occur and this precipitation may be due to the ion strength of the interstitial fluid combined with the presence of the acyl chain on the surface of the insulin, for example the insulin hexamer. Surprisingly, this reaction can be avoided when a formulation of an acylated insulin containing albumin is injected to a patient.

Below is an explanation of the interactions as they are presumed to take place. However, this invention is not limited to the interactions taking place exactly as outlined below.

The pharmaceutical formulation of this invention contains acylated insulin and albumin. Furthermore, the formulation of this invention may contain the following components: a buffer, a conservative, an isotonic agent, zinc acetate and/or a physical and/or a chemical stabiliser. Albumin has up to seven different lipid binding sites depending on the size and structure of the lipid. Acylated insulin can bind to albumin via the acyl chain to one or more of the albumin lipid binding sites. The invention is the surprising discovery that co-formulation with albumin can result in stabilisation of the acyl chain of acylated insulin thereby preventing or reducing unwanted reactions like precipitation and aggregation of the acylated insulin.

After injection to a patient of an acylated insulin formulation containing no albumin, acylated insulins may precipitate and/or aggregate as a result of ionic strength in the formulation or in the subcutis. The ion strength in the subcutis is about 150 mM sodium chloride which defines the concentration in an isotonic solution. Precipitation of acylated insulin in the subcutis can result in decreased predictability of the time of action of the acylated insulin and decreased the bioavailbility of the acylated insulin. One technical problem and pharmaceutical task is to make a pharmaceutical formulation of an acylated insulin with predictable bioavailability and time of action resulting in a reproducable blood glucose lowering profile for the diabetic patient. Furthermore, a pharmaceutical formulation which is designed to contain soluble acylated insulin in high ionic strength may have a limited shelf life, due to the physical precipitation of the acylated insulin in the formulation. A second technical problem is to make a physically stable pharmaceutical formulation containing acylated insulin in high ionic strength.

The technical solution to the two problems is that the presence of albumin in the formulations prevents acylated insulin to precipitate after injection, probably as a result of increase in ion strength, e.g., by injection in the subcutis.

The acylated insulin precipitation in 150 mM sodium chloride is avoided by addition of albumin to the formulation in a stoichiometric amount in the range from about 1 to about 10 moles of acylated insulins per mole albumin, preferably in the range from about 1 to about 6 moles of acylated insulins per mole albumin.

The insulin dimer formation constant is in micromolar range of human insulin. Acylated insulins with dimer formation constants in the same range as for human insulin forms dimers and the acyl chains of the acylated insulins interact with different albumin molecules in the ratio of two mole of acylated insulin to two moles of albumin complexes. When zinc atoms are present in the formulation, acylated insulin zinc hexamers can be formed and the acyl chains of these hexamers may interact with different albumin molecules in the formation of an insulin hexamer-albumin complexes. The pharmaceutical profile of a formulation with albumin and an acylated insulin zinc hexamer will, therefore, depend on the stoichiometric ratio between albumin and acylated insulin and the resulting existence of oligomers of acylated insulin hexamers with albumin molecules.

The chemical and physical stability of the acylated insulin in the formulation may, to a large degree, dependent on the formation of the R6 hexamer. Hence, the presence of at least two zinc ions, at least two chloride ions, and at least six phenol or cresol molecules per mole of acylated insulin is desirable. Such a formulation will, therefore, contain excess amounts of zinc acetate, sodium chloride, phenol and cresol. Since albumin can bind zinc, the chemically stable formulation with albumin will, preferably, contain from about 3 to about 7 zinc ions per 6 acylated insulin molecules which can ensure formation of the acylated insulin R6 hexamer and zinc albumin interaction. The chemical stability of albumin is limited by formation of albumin covalent dimers. For example, addition of stabilisers like sodium caprate and/or detergents like polysorbate 20 and polysorbate 80 reduce albumin dimer formation. The combined acylated insulin/albumin formulation may, therefore, contain sodium caprate and polysorbate in addition to zinc, phenol, cresol and sodium chloride.

Furthermore, it has surprisingly been found that the properties of the formulations of this invention can be improved if nicotinamide is added to the formulations. In one embodiment, the formulations of this invention contains from about 20 mM to about 200 mM of nicotinamide, optionally combined with from about 5 mM to about 50 mM arginine, and preferably from about 40 mM to about 150 mM of nicotinamide, optionally combined with from about 10 mM to about 30 mM arginine.

Even though this invention relates to a formulation containing albumin and an acylated insulin as defined herein wherein there is no covalent bond between albumin and said acylated insulin, said formulation may in a specific embodiment contain an acylated insulin to which albumin is bound covalently. In such an embodiment, the amino acid sequence of the acylated insulin may be the same or different from the amino acid sequence of the insulin to which albumin is bound covalently.

In a preferred embodiment of this invention, there is no precipitated material in the formulation of this invention. However, insulin formulations containing both insulin in dissolved form and insulin in non-dissolved (precipitated) form have been on the market for decades and are known to the skilled art worker. Hence, in one embodiment of this invention, the formulation contains both dissolved insulin and non-dissolved insulin.

The formulation can be made as follows: Acylated insulin powder is dissolved in Milli-Q water at pH 7.4. Phosphate buffer, zinc acetate, sodium chloride, phenol, cresol, glycerol and albumin may be added in the order listed or in any other desired or convenient order to yield the final concentrations designed for the formulation.

The degree of protraction is, to a certain degree, dependent on the molar ratio between the acylated insulin and albumin. Generally, a relatively larger amount of insulin will result in a more protracted rate of absorption, i.e., a longer duration of action, probably due to the larger size of the insulin-albumin aggregate.

In an embodiment of this invention, it relates to a pharmaceutical formulation containing an acylated insulin analogue and albumin in amounts defined by the insulin solubility meaning that it does not result in precipitation or precipitates only to a minor or inferior degree and wherein the insulin is not covalently bound to albumin.

In another embodiment of this invention, it relates to a pharmaceutical formulation containing an acylated insulin analogue and albumin in stoichiometric amounts defined by the pharmaceutical protraction profile meaning that it depends on the pharmaceutical protraction profile desired and wherein the insulin is not covalently bound to albumin or only bound to a minor degree.

As mentioned earlier, the novel formulation of this invention also contains albumin. Albumin can be albumin of any species, for example, human albumin or des1(Asp) human albumin, e.g. albagen. Preferably, the albumin is of recombinant origin.

In the formulation of this invention, the albumin is not covalently bound to other chemical molecules or albumin is only bound in an amount of about 5% (weight/weight) or less to such other molecules, preferably less than 2%, more preferred less than 1%. In one embodiment, the albumin is not covalently bound to the acylated insulin or only bound in an amount of about 5% (weight/weight) or less to the acylated insulin, preferably less than 2%, more preferred less than 1%.

In one embodiment, the acylated insulin is an insulin acylated in the $\epsilon$-amino group in the lysine side chain present in an amino acid extension of the C-terminal end of the A-chain of insulin and analogues thereof as disclosed in WO 2009/022005 or WO 2009/022013.

In another embodiment, the acylated insulin is selected from the following:

| Name | Alternative name |
|---|---|
| A22K($N^\epsilon$-Hexadecandioyl-(3-(2-{2-[2-(2-aminoethoxy)-ethoxy]ethoxy}ethoxy)propionyl-γGlu), B29R, desB30 human insulin | |
| A22K($N^\epsilon$-Hexadecandioyl-(2-aminoethyl-PEG2000-yl-acetyl)), B29R desB30 human insulin | |
| A22K($N^\epsilon$-3-(3-{4-[3-(5-Carboxypentanoylamino)propoxy]-butoxy}propylcarbamoyl)propionyl-γGlu), B29R, desB30 human insulin | |

-continued

| Name | Alternative name |
| --- | --- |
| A22K(Nᵉ-[2-(2-[2-(2-[2-(Octadecandioyl-γGlu)amino]-ethoxy)ethoxy]acetylamino)ethoxy)ethoxy)acetyl]), B29R, desB30 human insulin | A22K(Nᵉ(Octadecandioyl-γGlu-OEG-OEG)), B29R, desB30 human insulin |
| A22K(Nᵉ-3-(3-{4-[3-(13-Carboxytridecanoylamino)-propoxy]butoxy}propylcarbamoyl)propionyl-γGlu), B29R, desB30 human insulin | |
| A22K(Nᵉ-[2-(2-[2-(2-[2-(Eicosanedioyl-γGlu)amino]-ethoxy)ethoxy]acetylamino)ethoxy)ethoxy)acetyl]), B29R, desB30 human insulin | A22K(Nᵉ(Eicosanedioyl-γGlu-OEG-OEG)), B29R, desB30 human insulin |
| A14E, A22K(Nᵉ-[2-(2-[2-(2-[2-(Octadecandioyl-γGlu)-amino]ethoxy)ethoxy]acetylamino)ethoxy]ethoxy)acetyl]), B25H, B29R, desB30 human insulin | A14E, A22K(Nᵉ(Octadecandioyl-γGlu-OEG-OEG)), B25H, B29R, desB30 human insulin |
| A22K(Nᵉ-Octadecandioyl-γGlu-[2-(2-{2-[2-(2-amino-ethoxy)ethoxy]acetylamino}ethoxy)ethoxy]acetyl), desB29, desB30 human insulin | A22K(Nᵉ(Octadecandioyl-γGlu-OEG-OEG)), desB29, desB30 human insulin |
| A14E, A22K(Nᵉ-Eicosanedioyl-γGlu-(3-(2-{2-[2-(2-amino-ethoxy)ethoxy]ethoxy}ethoxy)propionyl)), B25H, B29R, desB30 human insulin | |
| A18L, A22K(Nᵉ-Octadecandioyl-γGlu-[2-(2-{2-[2-(2-aminoethoxy)ethoxy]acetylamino}ethoxy)ethoxy]acetyl), B29R, desB30 human insulin | A18L, A22K(Nᵉ(Octadecandioyl-γGlu-OEG-OEG)), B29R, desB30 human insulin |
| A8H, A22K(Nᵉ-Octadecandioyl-γGlu-[2-(2-{2-[2-(2-amino-ethoxy)ethoxy]acetylamino}ethoxy)ethoxy]acetyl), B29R, desB30 human insulin | A8H, A22K(Nᵉ(Octadecandioyl-γGlu-OEG-OEG)), B29R, desB30 human insulin |
| A22K(Nᵉ-Octadecandioyl-γGlu-[2-(2-{2-[2-(2-amino-ethoxy)ethoxy]acetylamino}ethoxy)ethoxy]acetyl-γGlu), B29R, desB30 human insulin | A22K(Nᵉ(Octadecandioyl-γGlu-OEG-OEG-γGlu)), B29R, desB30 human insulin |
| A22K(Nᵉ-Eicosanedioyl-γGlu-(3-{2-[2-(2-{2-[2-(2-amino-ethoxy)ethoxy]ethoxy}ethoxy)ethoxy]ethoxy}propionyl)), B29R, desB30 human Insulin | |
| A22K(Nᵉ-Octadecandioyl-γGlu-(3-(2-{2-[2-(2-amino-ethoxy)ethoxy]ethoxy}ethoxy)propionyl)), B29R, desB30 human insulin | |
| A14E, A22K(Nᵉ-Octadecandioyl-γGlu-(3-[2-(2-{2-[2-(2-{2-[2-(2-aminoethoxy)ethoxy]ethoxy}ethoxy)ethoxy]ethoxy}-ethoxy)ethoxy]propionyl)), B25H, B29R, desB30 human insulin | |
| A14E, A22K(Nᵉ-Eicosanedioyl-γGlu-γGlu-(3-[2-(2-{2-[2-(2-{2-[2-(2-aminoethoxy)ethoxy]ethoxy}ethoxy)ethoxy]-ethoxy}ethoxy)ethoxy]propionyl)), B25H, B29R, desB30 human insulin | |
| A14E, A22K(Nᵉ-Octadecandioyl-γGlu-(3-(2-{2-[2-(2-aminoethoxy)ethoxy]ethoxy}ethoxy)propionyl-γGlu), B25H, B29R, desB30 human insulin | |
| A22K(Nᵉ-Octadecandioyl-γGlu-[2-(2-{2-[2-(2-amino-ethoxy)ethoxy]acetylamino}ethoxy)ethoxy]acetyl), B28E, B29R, desB30 human insulin | A22K(Nᵉ(Octadecandioyl-γGlu-OEG-OEG)), B28E, B29R, desB30 human insulin |
| A22K(Nᵉ-Octadecandioyl-γGlu-[2-(2-{2-[2-(2-{2-[2-(2-aminoethoxy)ethoxy]acetylamino}ethoxy)ethoxy]acetyl-amino}ethoxy)ethoxy]acetyl), B29R, desB30 human insulin | A22K(Nᵉ-Octadecandioyl-γGlu-OEG-OEG-OEG)), B29R, desB30 human insulin |
| A14E, A22K(Nᵉ-[2-(2-[2-(2-[2-(Eicosanedioyl-γGlu)-amino]ethoxy)ethoxy]acetylamino)ethoxy)ethoxy)acetyl]), B25H, B29R, desB30 human insulin | A14E, A22K(Nᵉ(Eicosanedioyl-γGlu-OEG-OEG)), B25H, B29R, desB30 human insulin |
| A22K(Nᵉ-Octadecandioyl-(3-(2-{2-[2-(2-aminoethoxy)-ethoxy]ethoxy}ethoxy)propionyl-γGlu), B29R, desB30 human insulin | |
| A22K(Nᵉ-Eicosanedioyl-(3-(2-{2-[2-(2-aminoethoxy)-ethoxy]ethoxy}ethoxy)propionyl-γGlu), B29R, desB30 human insulin | |
| A22K(Nᵉ-Octadecandioyl-(2-aminoethyl-PEG2000-yl-acetyl)), B29R desB30 human insulin | |
| A22K(Nᵉ-Eicosanedioyl-(2-aminoethyl-PEG2000-yl-acetyl)), B29R desB30 human insulin | |
| A22K(Nₑ-3-(3-{4-[3-(15-Carboxypentadecanoylamino)-propoxy]butoxy}propylcarbamoyl)propionyl-γGlu), B29R desB30 human insulin | |
| A22K(Nₑ-3-(3-{4-[3-(17-Carboxyheptadecanoylamino)-propoxy]butoxy}propylcarbamoyl)propionyl-γGlu), B29R desB30 human insulin | |
| A22K(Nᵉ-Tetradecandioyl-(3-(2-{2-[2-(2-aminoethoxy)-ethoxy]ethoxy}ethoxy)propionyl-γGlu), B29R, desB30 human insulin | |
| A8H, A22K(Nᵉ-Octadecandioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A8H, A22K(Nᵉ(Octadecandioyl-γGlu-OEG-OEG)), B29R, desB30 human insulin |

-continued

| Name | Alternative name |
|---|---|
| A18L, A22K(Nᵉ-Octadecandioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A18L, A22K(Nᵉ(Octadecandioyl-γGlu-OEG-OEG)), B29R, desB30 human insulin |
| A22K(Nᵉ-Octadecandioyl-γGlu-[2-(2-{2-[2-(2-{2-[2-(2-{2-[2-(2-aminoethoxy)ethoxy]acetylamino}ethoxy)ethoxy]-acetylamino}ethoxy)ethoxy]acetylamino}ethoxy)ethoxy]-acetyl), B29R, desB30 human insulin | |
| A8H, A22K(Nᵉ-Octadecandioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A8H, A22K(Nᵉ(Octadecandioyl-γGlu-OEG-OEG-OEG)), B29R, desB30 human insulin |
| A18L, A22K(Nᵉ-Octadecandioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A18L, A22K(Nᵉ(Octadecandioyl-γGlu-OEG-OEG-OEG)), B29R, desB30 human insulin |
| A8H, A22K(Nᵉ-Eicosanedioyl-γGlu-[2-(2-{2-[2-(2-{2-[2-(2-aminoethoxy)ethoxy]acetylamino}ethoxy)ethoxy]acetyl-amino}ethoxy)ethoxy]acetyl), B29R, desB30 human insulin | A8H, A22K(Nᵉ(Eicosanedioyl-γGlu-OEG-OEG-OEG)), B29R, desB30 human insulin |
| A8H, A22K(Nᵉ-Eicosanedioyl-γGlu-[2-(2-{2-[2-(2-{2-[2-(2-aminoethoxy)ethoxy]acetylamino}ethoxy)ethoxy]acetyl-amino}ethoxy)ethoxy]acetyl), B29R, desB30 human insulin | |
| A18L, A22K(Nᵉ-Eicosanedioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A18L, A22K(Nᵉ(Eicosanedioyl-γGlu-OEG-OEG-OEG)), B29R, desB30 human insulin |
| A22K(Nᵉ-Eicosanedioyl-γGlu-[2-(2-{2-[2-(2-{2-[2-(2-{2-[2-(2-aminoethoxy)ethoxy]acetylamino}ethoxy)ethoxy]-acetylamino}ethoxy)ethoxy]acetylamino}ethoxy)ethoxy]-acetyl), B29R, desB30 human insulin | A22K(Nᵉ(Eicosanedioyl-γGlu-OEG-OEG-OEG-OEG)), B29R, desB30 human insulin |
| A8H, A22K(NᵉEicosanedioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A8H, A22K(Nᵉ(Eicosanedioyl-γGlu-OEG-OEG-OEG-OEG)), B29R, desB30 human insulin |
| A18L, A22K(Nᵉ-Eicosanedioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A18L, A22K(Nᵉ(Eicosanedioyl-γGlu-OEG-OEG-OEG-OEG)), B29R, desB30 human insulin |
| A8H, A22K(Nᵉ-Hexadecanedioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A8H, A22K(Nᵉ(Hexadecanedioyl-γGlu-OEG-OEG-OEG)), B29R, desB30 human insulin |
| A8H, A22K(Nᵉ-Hexadecanedioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A8H, A22K(Nᵉ(Hexadecanedioyl-γGlu-OEG-OEG-OEG)), B29R, desB30 human insulin |
| A18L, A22K(Nᵉ-Hexadecanedioyl-γGlu-[2-(2-{2-[2-(2-{2-[2-(2-aminoethoxy)ethoxy]acetylamino}ethoxy)ethoxy]-acetylamino}ethoxy)ethoxy]acetyl), B29R, desB30 human insulin | A18L, A22K(Nᵉ(Hexadecanedioyl-γGlu-OEG-OEG-OEG)), B29R, desB30 human insulin |
| A22K(Nᵉ-Hexadecanedioyl-γGlu-[2-(2-{2-[2-(2-{2-[2-(2-{2-[2-(2-aminoethoxy)ethoxy]acetylamino}ethoxy)ethoxy]-acetylamino}ethoxy)ethoxy]acetylamino}ethoxy)ethoxy]-acetyl), B29R, desB30 human insulin | A22K(Nᵉ(Hexadecanedioyl-γGlu-OEG-OEG-OEG)), B29R, desB30 human insulin |
| A8H, A22K(Nᵉ-Hexadecanedioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A8H, A22K(Nᵉ(Hexadecanedioyl-γGlu-OEG-OEG-OEG-OEG)), B29R, desB30 human insulin |
| A18L, A22K(Nᵉ-Hexadecanedioyl-γGlu-[2-(2-{2-[2-(2-{2-[2-(2-{2-[2-(2-aminoethoxy)ethoxy]acetylamino}ethoxy)-ethoxy]acetylamino}ethoxy)ethoxy]acetylamino}ethoxy)-ethoxy]acetyl), B29R, desB30 human insulin | A18L, A22K(Nᵉ(Hexadecanedioyl-γGlu-OEG-OEG-OEG-OEG)), B29R, desB30 human insulin |
| A22K(Nᵉ-Hexadecanedioyl-γGlu-[2-(2-{2-[2-(2-amino-ethoxy)ethoxy]acetylamino}ethoxy)ethoxy]acetyl), B29R, desB30 human insulin | A22K(Nᵉ(Hexadecanedioyl-γGlu-OEG-OEG)), B29R, desB30 human insulin |
| A8H, A22K(Nᵉ-Hexadecanedioyl-γGlu-[2-(2-{2-[2-(2-aminoethoxy)ethoxy]acetylamino}ethoxy)ethoxy]acetyl), B29R, desB30 human insulin | A8H, A22K(Nᵉ(Hexadecanedioyl-γGlu-OEG-OEG)), B29R, desB30 human insulin |
| A18L, A22K(Nᵉ-Hexadecanedioyl-γGlu-[2-(2-{2-[2-(2-aminoethoxy)ethoxy]acetylamino}ethoxy)ethoxy]acetyl), B29R, desB30 human insulin | A18L, A22K(Nᵉ(Hexadecanedioyl-γGlu-OEG-OEG)), B29R, desB30 human insulin |

Albumin can be covalently bound to an acylated insulin. However, it is important that, in the formulations of this invention, no or less than 5% of the albumin is covalently bound to the acylated insulin. The skilled art worker knows how to bind albumin covalently to insulin. For example, albumin can be covalently bound to insulin by the use of cross-linking reagents, e.g., aldehydes and N-hydroxysuccinimide esters. The skilled art worker also knows how to avoid that albumin binds covalently to insulin. If, for example, acylated insulin having no reactive groups and albumin are mixed at room temperature and at a neutral pH values, e.g., about 7, no covalent binding is expected to take place between the acylated insulin and albumin.

Furthermore, the formulation of this invention may contain other ingredients commonly used in insulin formulations. Examples of such ingredients are buffers, for example, acetate, citrate, phosphates, malonic acid, arginine or TRIS, preservatives, for example, phenol, m-cresol or methyl 4-hydroxy-benzoate, zinc ions and an acid or a base used to regulate the pH value, for example hydrochloric acid or sodium hydroxide, isotonic agents, for example, glycerol, mannitol or propyleneglycol, stabilisers, for example, polysorbate 20, polysorbate 80 or sodium caprate.

Injection devices are syringes which more and more frequently are pen like devices. Another sort of injection devices is pump devices which are placed on the body and which are stationary for days or weeks.

The formulation of this invention is used analogously to the use of known insulin formulations. The physician is familiar with the treatment of patients with diabetes and the physician will know how to use the formulation of this invention, i.e., analogously with the administration of other insulin formulations. Also, the physician and many diabetic patients will know how to inject the novel formulations.

Preferred Features of this Invention

To sum up and supplement the above statements, the features of this invention are as follows:

1. An injectable pharmaceutical formulation containing an acylated insulin and albumin characterized in that at least 80% (weight/weight) of the acylated insulin is dissolved and wherein not more than 5% (weight/weight) of the insulin is covalently bound to albumin.
2. An pharmaceutical formulation containing an acylated insulin and albumin wherein at least 80% (weight/weight) of the acylated insulin is dissolved and wherein not more than 5% (weight/weight) of the insulin is covalently bound to albumin for use by injection.
3. A pharmaceutical, optionally injectable, formulation according to any one of the preceding clauses, wherein the acylated insulin is a salting out, acylated insulin.
4. A pharmaceutical, optionally injectable, formulation according to any one of the preceding clauses, wherein the salting out, acylated insulin is an acylated insulin which has a solubility in a 150 mM NaCl solution containing three zinc ions per six insulin molecules of below 30%, as defined specifically in Test A herein, preferably above 50% in a 150 M sodium chloride solution containing three zinc ions per six insulin molecules and most preferred above 60% in a 150 mM sodium chloride solution containing three zinc ions per six insulin molecules.
5. A pharmaceutical, optionally injectable, formulation according to any one of the preceding clauses to the extent possible, wherein the salting out, acylated insulin is an acylated insulins which forms an insulin-albumin-oligomer with a molecular weight above 440,000, as defined specifically in Test B herein.
6. A pharmaceutical, optionally injectable, formulation according to any one of the preceding clauses to the extent possible, wherein the salting out, acylated insulin is an acylated insulin which has a solubility in a 150 mM NaCl solution not containing zinc of below 30%, as defined specifically in Test C herein.
7. A pharmaceutical, optionally injectable, formulation according to any one of the preceding clauses, to the extent possible, wherein the salting out, acylated insulin is an acylated insulin mentioned specifically in WO 07/096431, i.e., the compounds mentioned therein with the names $N^{\epsilon A8}$-myristyl LysA8 ArgB29 desB30 human insulin, $N^{\epsilon A9}$-myristyl LysA9 ArgB29 desB30 human insulin, $N^{\epsilon A10}$-myristyl LysA10 ArgB29 desB30 human insulin, $N^{\epsilon A12}$-myristyl LysA12 ArgB29 desB30 human insulin, $N^{\epsilon A14}$-myristyl LysA14 ArgB29 desB30 human insulin, $N^{\epsilon A15}$-myristyl LysA15 ArgB29 desB30 human insulin, $Ar^{\epsilon A17}$-myristyl LysA17 ArgB29 desB30 human insulin, $N^{\epsilon A18}$-myristyl LysA18 ArgB29 desB30 human insulin, $N^{\epsilon A21}$-myristyl LysA21 ArgB29 desB30 human insulin, $N^{\epsilon A22}$-myristyl LysA22 ArgB29 desB30 human insulin, $N^{\epsilon B1}$-myristyl LysB1 ArgB29 desB30 human insulin, $N^{\epsilon B2}$-myristyl LysB2 ArgB29 desB30 human insulin, $N^{\epsilon B3}$-myristyl LysB3 ArgB29 desB30 human insulin, $N^{\epsilon B4}$-myristyl LysB4 ArgB29 desB30 human insulin, $N^{\epsilon B20}$-myristyl LysB20 ArgB29 desB30 human insulin, $N^{\epsilon B21}$-myristyl LysB21 ArgB29 desB30 human insulin, $N^{\epsilon B22}$-myristyl LysB22 ArgB29 desB30 human insulin, $N^{\epsilon A6}$-ω-carboxypentadecanoyl-γ-Glu LysA8 ArgB29 desB30 human insulin, $N^{\epsilon A9}$-ω-carboxy-pentadecanoyl-γ-Glu LysA9 ArgB29 desB30 human insulin, $N^{\epsilon A10}$-ω-carboxypentadecanoyl-γ-Glu LysA10 ArgB29 desB30 human insulin, $N^{\epsilon A12}$-ω-carboxy-pentadecanoyl-γ-Glu LysA12 ArgB29 desB30 human insulin, $N^{\epsilon A14}$-ω-carboxypentadecanoyl-γ-Glu LysA14 ArgB29 desB30 human insulin, $N^{\epsilon A15}$-ω-carboxypentadecanoyl-γ-Glu LysA15 ArgB29 desB30 human insulin, $N^{\epsilon A17}$-ω-carboxypentadecanoyl-γ-Glu LysA17 ArgB29 desB30 human insulin, $N^{\epsilon A18}$-ω-carboxypentadecanoyl-γ-Glu LysA18 ArgB29 desB30 human insulin, $N^{\epsilon A21}$-ω-carboxy-pentadecanoyl-γ-Glu LysA21 ArgB29 desB30 human insulin, $N^{\epsilon A22}$-ω-carboxypentadecanoyl-γ-Glu LysA22 ArgB29 desB30 human insulin, $N^{\epsilon B1}$-ω-carboxypentadecanoyl-γ-Glu LysB1 ArgB29 desB30 human insulin, $N^{\epsilon B2}$-ω-carboxypentadecanoyl-γ-Glu LysB2 ArgB29 desB30 human insulin, $N^{\epsilon B3}$-ω-carboxypentadecanoyl-γ-Glu LysB3 ArgB29 desB30 human insulin, $N^{\epsilon B4}$-ω-carboxypenta-decanoyl-γ-Glu LysB4 ArgB29 desB30 human insulin, $N^{\epsilon B20}$-ω-carboxypentadecanoyl-γ-Glu LysB20 ArgB29 desB30 human insulin, $N^{\epsilon B21}$-ω-carboxypentadecanoyl-γ-Glu LysB21 ArgB29 desB30 human insulin, $N^{\epsilon B22}$-ω-carboxypentadecanoyl-γ-Glu LysB22 ArgB29 desB30 human insulin, $N^{\epsilon A22}$-ω-carboxypentadecanoyl-γ-Glu LysA22 GlyA21 ArgB29 desB30 human insulin, $N^{\epsilon A22}$-ω-carboxypentadecanoyl-γ-Glu LysA22 AlaA21 ArgB29 desB30 human insulin, $N^{\epsilon A22}$-ω-carboxy-pentadecanoyl-γ-Glu LysA22 GlnA21 ArgB29 desB30 human insulin, $N^{\epsilon A23}$-ω-carboxypentadecanoyl-γ-Glu LysA23 GlyA21 GlyA22 ArgB29 desB30 human insulin, $N^{\epsilon A23}$-ω-carboxypenta-decanoyl-γ-Glu LysA23 AlaA21 GlyA22 ArgB29 desB30 human insulin, $N^{\epsilon A23}$-ω-carboxypenta-decanoyl-γ-Glu LysA23 GlnA21 GlyA22 ArgB29 desB30 human insulin, $N^{\epsilon A24}$-ω-carboxypenta-decanoyl-γ-Glu LysA24 GlyA21 GlyA22 GlyA23 ArgB29 desB30 human insulin, $N^{\epsilon A24}$-ω-carboxy-pentadecanoyl-γ-Glu LysA24 AlaA21 GlyA22 GlyA23 ArgB29 desB30 human insulin, $N^{\epsilon A24}$-ω-carboxypentadecanoyl-γ-Glu LysA24 GlnA21 GlyA22 GlyA23 ArgB29 desB30 human insulin, $N^{\epsilon A22}$-ω-carboxyheptadecanoyl-γ-Glu LysA22 ArgB29 desB30 human insulin, $N^{\epsilon A23}$-ω-carboxy-hepentadecanoyl-γ-Glu LysA23 GlyA22 ArgB29 desB30 human insulin, $N^{\epsilon A23}$-ω-carboxyhepta-decanoyl-γ-Glu LysA23 GlyA21 GlyA22 ArgB29 desB30 human insulin, $N^{\epsilon A23}$-ω-carboxyheptadecanoyl-γ-Glu LysA23 AlaA21 GlyA22 ArgB29 desB30 human insulin, $N^{\epsilon A23}$-ω-carboxyhepta-decanoyl-γ-Glu LysA23 GlnA21 GlyA22 ArgB29 desB30 human insulin, $N^{\epsilon A24}$-ω-carboxyhepta-decanoyl-γ-Glu LysA24 GlyA21 GlyA22 GlyA23 ArgB29 desB30 human insulin, $N^{\epsilon A24}$-ω-carboxy-heptadecanoyl-γ-Glu LysA24 AlaA21 GlyA22 GlyA23 ArgB29 desB30 human insulin, $N^{\epsilon A24}$-ω-carboxyhentadecanoyl-γ-Glu LysA24 GlnA21 GlyA22 GlyA23 ArgB29 desB30 human insulin, $N^{\epsilon A22}$-3-carboxy-5-hexadecandioylaminobenzoyl LysA22 ArgB29 desB30 human insulin, $N^{\epsilon A22}$-3-carboxy-5-octadecandioylaminobenzoyl LysA22 ArgB29 desB30 human insulin, $N^{\epsilon A22}$-10-(3,5-di-carboxyphenoxy)decanoyl-γ-Glu LysA22 ArgB29 desB30 human insulin and $N^{\epsilon A22}$-4-[10-(3,5-dicarboxyphenoxy)decanoylamino]butyryl LysA22 ArgB29 desB30 human insulin.

8. A pharmaceutical, optionally injectable, formulation according to any one of the preceding clauses, to the extent possible, wherein the salting out, acylated insulin is any of the acylated insulins mentioned in the above table.

9. A formulation, according to any one of the preceding clauses to the extent possible wherein at least 85% (weight/weight) of the acylated insulin is dissolved.

10. A formulation, according to any one of the preceding clauses to the extent possible wherein at least 90% (weight/weight) of the acylated insulin is dissolved.

11. A formulation, according to any one of the preceding clauses to the extent possible wherein at least 95% (weight/weight) of the acylated insulin is dissolved.

12. A formulation according to any one of the preceding clauses to the extent possible wherein at least 99% (weight/weight) of the acylated insulin is dissolved.

13. A formulation according to any one of the preceding clauses to the extent possible wherein at least 99.9% (weight/weight) of the acylated insulin is dissolved.

14. A formulation according to the preceding clause wherein all the acylated insulin is dissolved.

15. A formulation according to any one of the preceding clauses to the extent possible wherein not more than 1% (weight/weight) of the acylated insulin is covalently bound to albumin.

16. A formulation according to any one of the preceding clauses to the extent possible wherein not more than 0.1% (weight/weight) of the acylated insulin is covalently bound to albumin.

17. A formulation according to any one of the preceding clauses to the extent possible wherein no insulin is covalently bound to albumin.

18. A formulation according to any one of the preceding clauses to the extent possible wherein the molar ratio between albumin and acylated insulin is in the range from about 1:3 to about 1:10, preferably from about 1:5 to about 1:7.

19. A formulation according to any one of the preceding clauses which is injectable.

20. A formulation according to any one of the preceding clauses which is isotonic.

21. A formulation according to any one of the preceding use clause to the extent possible, characterized in that the acylated insulin is A22K($N^\epsilon$(eicosanedioyl-gGlu-OEG-OEG)), B29R, desB30 human insulin.

22. A formulation according to any one of the preceding clauses to the extent possible, characterized in that the albumin is human serum albumin or Albagen.

23. A formulation according to any one of the preceding clauses to the extent possible, characterized in that the albumin is human serum albumin.

24. A formulation according to any one of the preceding clauses to the extent possible containing sodium chloride, preferably in an amount in the range from about 2 to about 50 mM, preferably from about 5 to about 20 mM.

25. A formulation according to any one of the preceding clauses to the extent possible containing glycerol, in the range from about 20 to about 200 mM, preferably from about 50 to about 200 mM, even more preferred about 174 mM.

26. A formulation according to any one of the preceding clauses to the extent possible containing zinc ions, preferably in an amount in the range from about two zinc atoms per six acylated insulin molecules to about 10 zinc atoms per 6 acylated insulin molecules, preferably from about three zinc atoms per six acylated insulin molecules to about 6 zinc atoms per 6 acylated insulin molecules.

27. A formulation according to any one of the preceding clauses to the extent possible containing phenol, preferably in an amount in the range from about 5 to about 60 mM, more preferred from about 8 to about 30 mM, preferably from about 10 to about 20 mM.

28. A formulation according to any one of the preceding clauses to the extent possible containing m-cresol, preferably in an amount in the range from about 5 to about 50 mM, more preferably from about 8 to about 30 mM, preferably from about 10 to about 20 mM.

29. A formulation according to any one of the preceding clauses to the extent possible containing sodium caprate, preferably in an amount in the range from about 2 to about 50 mM, more preferred from about 5 to about 30 mM.

30. A formulation according to any one of the preceding clauses to the extent possible containing polysorbate 20, preferably in an amount in the range from about 0.001% to about 0.1%, preferably from about 0.005% to about 0.05%.

31. A formulation according to any one of the preceding clauses to the extent possible containing polysorbate 80, preferably in an amount in the range from about 0.001% to about 0.1%, preferably from about 0.005% to about 0.05%.

32. A formulation according to any one of the preceding clauses to the extent possible containing nicotinamide, preferably in an amount in the rage from about 10 mM to about 200 mM, more preferred in the range from about 20 mM to about 200 mM and even more preferred in the range from about 40 mM to about 150 mM.

33. A formulation according to any one of the preceding clauses to the extent possible containing arginine, preferably in an amount in the rage from about 5 mM to about 50 mM, more preferred in the range from about 10 mM to about 30 mM.

34. A formulation as described in any one of the above, specific examples.

35. A formulation according to any one of the preceding clauses for subcutaneous administration.

36. The use of albumin to avoid precipitation or avoid precipitation in an inferior or minor amount in a pharmaceutical, aqueous solution of an acylated insulin after subcutaneous injection, characterized in that albumin is added to said aqueous solution of an acylated insulin before the solution is injected subcutaneously.

37. The use according to the preceding clause, characterized in that said solution is isotonic.

38. The use according to any one of the preceding use clauses, characterized in that said solution is isotonic.

39. The use according to any one of the preceding use clause to the extent possible, characterized in that the acylated insulin is A22K(N(eps)-eicosanedioyl-gGlu-OEG-OEG)), B29R, desB30 human insulin.

40. The use of an acylated insulin and albumin for the manufacture of a medicament for the prevention or treatment of diabetes by injection characterized in that the solution to be injected contains an acylated insulin and albumin according to any of the preceding clauses.
41. A method of treating or preventing diabetes, the method comprising administering to a subject in need thereof a therapeutically effective amount of an injectable pharmaceutical formulation containing an acylated insulin and albumin wherein at least 95% (weight/weight) of the insulin is dissolved and wherein not more than 5% (weight/weight) of the insulin is covalently bound to albumin and, preferably, said formulation is as defined in any of the above product clauses.
42. Any novel feature or combination of features described herein.

Combining one or more of the clauses and embodiments described herein, optionally also with one or more of the claims below, results in further embodiments and the present invention relates to all possible combinations of said clauses, embodiments and claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (vide, EPO guidelines C, III, 4.13).

This invention includes all modifications and equivalents of the subject matter recited in the claims and clauses appended hereto as permitted by applicable law.

The following examples are offered by way of illustration, not by limitation.

The abbreviations used are as follows: HSA is human serum albumin.

EXAMPLE 1

Figure 2:
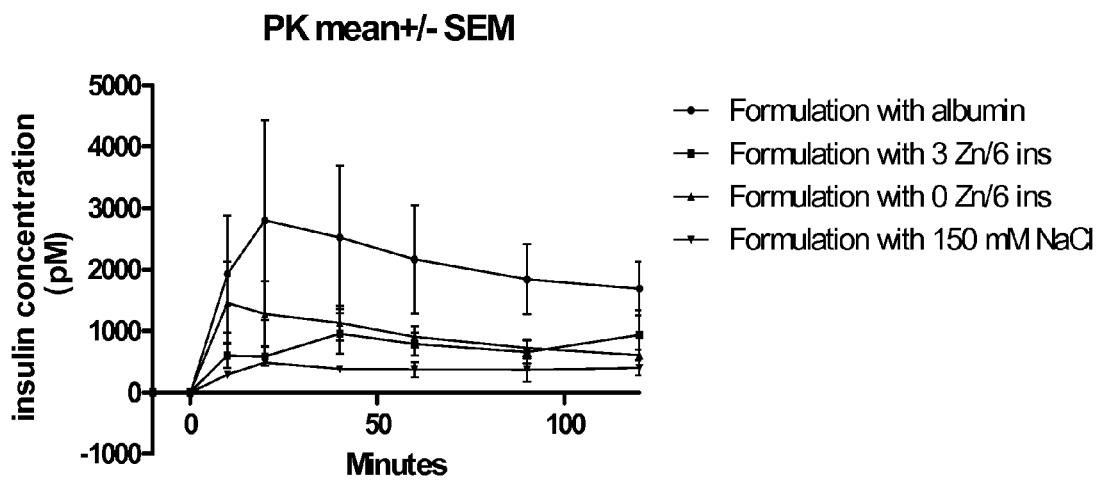
FIG. 2 is a graph showing the measured blood insulin concentration the first 100 minutes after injection.

Pigs were given equal amounts of A22K(N$^\epsilon$(eicosanedioyl-γGlu-OEG-OEG)), B29R, desB30 human insulin, by subcutaneous administration. The concentration of insulin in the blood was measured after injection and the result is shown in FIGS. 1 and 2. The graph in FIG. 1 show the measured insulin concentration from time 0 to 1500 minutes after injection and the graph in FIG. 2 shows the measured insulin concentration the first 100 minutes after injection. In the figures, the following abbreviations are used: "ins" is insulin, "PK" is pharmacokinetic, and "SEM" is standard error mean value. The following formulations were investigated:
1a): 300 uM A22K(N$^\epsilon$(eicosanedioyl-γGlu-OEG-OEG)), B29R, desB30 human insulin, 7 mM phosphate, pH 7.4, 300 μM pig serum albumin, 150 mM NaCl, 0 Zn/hexamer insulin (designated "Formulation with Albumin" in FIGS. 1 & 2).
1b): 600 uM A22K(N$^\epsilon$(eicosanedioyl-γGlu-OEG-OEG)), B29R, desB30 human insulin, 7 mM phosphate, pH 7.4, 174 mM glycerol, 30 mM phenol, 3 Zn/hexamer insulin (designated "Formulation with 3 Zn/6 ins" in FIGS. 1 & 2).
1c): 600 uM A22K(N$^\epsilon$(eicosanedioyl-γGlu-OEG-OEG)), B29R, desB30 human insulin, 7 mM phosphate, pH 7.4, 174 mM glycerol, 0 Zn/6 insulin molecules (designated "Formulation with 0 Zn/6 ins" in FIGS. 1 & 2).
1d): 600 uM A22K A22K(N$^\epsilon$(eicosanedioyl-γGlu-OEG-OEG)), B29R, desB30 human insulin, 7 mM phosphate, pH 7.4, 150 mM NaCl, 0 Zn/6 insulin molecules (designated "Formulation with 150 mM NaCl" in FIGS. 1 & 2).

The conclusions from the above investigation are as follows:

Acylated insulin in suspension with isotonic sodium chloride results in the lowest insulin concentration in the blood of the four formulations.

Soluble acylated insulin with and without zinc in the formulation, results in comparable insulin concentrations in the blood.

Soluble acylated insulin co-formulated with pig albumin and isotonic sodium chloride, result in the highest insulin concentration the blood, i.e., more than twice as high than the other three formulations. Co-formulation with albumin is seen to increase the bioavailability of acylated insulin and prevent precipitation of the acylated insulin in isotonic sodium chloride.

EXAMPLE 2

A solution of 45 μl 660 uM A22K(N$^\epsilon$(eicosanedioyl-γGlu-OEG-OEG)), B29R, desB30 human insulin (abbreviated to A22K(N(eps)eicosanedioyl) in table 1) in formulation according to Table 1 was mixed with 5 μl l of sodium chloride solution in concentration according to Table 1. 48 hours after the two solutions were mixed, the amount of precipitated acylated insulin was determined after filtration. The determination of the concentration was carried out by HPLC measurement of insulin in solution. The percentage amount of soluble acylated insulin in relation to the total amount of acylated insulin present in the test solution must be above 30% at a sodium chloride concentration of 150 mM, preferably above 50% at 150 M sodium chloride and most preferred above 60% at 150 mM.

TABLE 1

| Formulation: 600 μM insulin, 7 mM phosphate pH 7.4, 30 mM phenol | NaCl concentration, in mM | % insulin in solution |
|---|---|---|
| Human insulin, 3 Zn/6 insulin | 0 | 100 |
| | 5 | 76 |
| | 10 | 92 |
| | 25 | 75 |
| | 50 | 75 |
| | 75 | 86 |
| | 100 | 98 |
| | 125 | 87 |
| | 150 | 84 |
| | 175 | 78 |
| | 200 | 84 |
| A22K(N(eps)eicosanedioyl, 0 Zn/6 insulin | 0 | 97 |
| | 5 | 82 |
| | 10 | 81 |
| | 25 | 75 |

TABLE 1-continued

| Formulation: 600 μM insulin, 7 mM phosphate pH 7.4, 30 mM phenol | NaCl concentration, in mM | % insulin in solution |
|---|---|---|
| | 50 | 62 |
| | 75 | 44 |
| | 100 | 28 |
| | 125 | 20 |
| | 150 | 12 |
| | 175 | 0 |
| | 200 | 0 |
| A22K(N(eps)eicosanedioyl, 3 Zn/6 insulin | 0 | 71 |
| | 5 | 66 |
| | 10 | 70 |
| | 25 | 71 |
| | 50 | 74 |
| | 75 | 90 |
| | 100 | 50 |
| | 125 | 34 |
| | 150 | 23 |
| | 175 | 0 |
| | 200 | 0 |
| A22K(N(eps)eicosanedioyl, 0 Zn/6 insulin, 600 μM HSA | 0 | 77 |
| | 5 | 75 |
| | 10 | 77 |
| | 25 | 65 |
| | 50 | 63 |
| | 75 | 70 |
| | 100 | 84 |
| | 125 | 68 |
| | 150 | 100 |
| | 175 | 66 |
| | 200 | 77 |
| A22K(N(eps)eicosanedioyl 3 Zn/6 insulin, 600 μM HSA | 0 | 95 |
| | 5 | 86 |
| | 10 | 71 |
| | 25 | 91 |
| | 50 | Nd |
| | 75 | Nd |
| | 100 | Nd |
| | 125 | 89 |
| | 150 | 91 |
| | 175 | 71 |
| | 200 | 80 |

The conclusion from the above investigation is as follows:

The investigation of the solubility of A22K(N$^\epsilon$(eicosanedioyl-γGlu-OEG-OEG)), B29R, desB30 human insulin in increasing amounts of sodium chloride show that the presence of albumin prevents the otherwise observed insulin precipitation at 150 mM sodium chloride (isotonicity). A non-acylated insulin like human insulin is not precipitated at isotonic sodium chloride. Furthermore, the solubility of A22K(N$^\epsilon$(eicosanedioyl-γGlu-OEG-OEG)), B29R, desB30 human insulin is higher in the presence of zinc than in the absence of zinc.

EXAMPLE 3

A solution of 500 μl of A22K(N$^\epsilon$(eicosanedioyl-γGlu-OEG-OEG)), B29R, desB30 human insulin in formulation according to Table 2 was mixed with sodium chloride solution or glycerol in concentration according to Table 2 yielding a final insulin concentration of 600 μM. One hour after the two solutions were mixed, the solubility of the acylated insulin was judged by eye, visual inspection, determination of precipitation. The recovery of the insulin and the size of the insulin-albumin complexes formed in the samples were measured by native gelfiltration (size exclusion chromatography, see method description below). Only samples containing glycerol as isotonic agent were characterised by native gelfiltration. The recovery of acylated insulin with and without albumin was measured as the area of the chromatographic peak relative to the area of dilution rows of albumin standards.

Size Exclusion Chromatography (SEC), method description: SEC by non dissociating eluent to measure multihexamers larger than dihexamer (>albumin size). Superose 6PC 3.2/30 (GE life-sciences) 3.2×300 mm ($V_T$=2.4 ml) was eluted by isotonic saline (NaCl 140 mM+tris/HCl 10 mM+sodium azide 0.01%, pH 7.7 at 23° C. corresponding to 7.3 at 37° C.) at 80 μL/min and 37° C. UV detection was performed at 276 nm, and injection volume of 20 μL (22.7 μL loop) was used as standard injection volume (0.9% of total column volume). Run time of 32 min was used followed by an equilibration time of 48 min to elute phenol+m-cresol (total run time 80 min). Compare plot 6-32 min. The size of the insulin-albumin complexes were estimated from the retention times of the protein markers: thyroglobulin, Mw 669 kDa, ferritin, Mw 440 kDa, human serum albumin, Mw 60 kDa, ovalbumin 44 kDa, Cobalt insulin hexamer, Mw 36 kDa, insulin monomer, Mw 6 kDa.

TABLE 2

| Formulation: 600 μM A22K(N$^\epsilon$(eicosanedioyl-gGlu-OEG-OEG)), B29R, desB30 human insulin 7 mM phosphate pH 7.4 30 mM phenol | Isotonic Agent 174 mM glycerol or 150 mM NaCl | Insulin precipitate | SEC gelfiltration Recovery | SEC gelfiltration Retention time in min | SEC gelfiltration estimation of Mw (kDa) |
|---|---|---|---|---|---|
| 3 Zn/6 insulin | Glycerol | No | 20% | Nd | Nd |
| | NaCl | Yes | | | |
| 3 Zn/6 insulin, 200 μM HSA | Glycerol | No | 100% | 22.6 | 70 |
| | NaCl | No | | | |
| 3 Zn/6 insulin, 120 μM HSA | Glycerol | No | 100% | 19.7 | 440 |
| | NaCl | No | | | |
| 3 Zn/6 insulin, 80 μM HSA | Glycerol | No | 100% | 17.6 | 669 |
| | NaCl | No | | | |
| 3 Zn/6 insulin, 60 μM HSA | Glycerol | No | 100% | 17.6 | 669 |
| | NaCl | yes | | | |
| 3 Zn/6 insulin, 30 μM HSA | Glycerol | No | Nd | Nd | Nd |
| | NaCl | yes | | | |
| 0 Zn/6 insulin | Glycerol | No | 20% | Nd | Nd |
| | NaCl | Yes | | | |
| 0 Zn/6 insulin, 200 μM HSA | Glycerol | No | 100% | 21.7 | 130 |
| | NaCl | No | | | |
| 0 Zn/6 insulin, 120 μM HSA | Glycerol | No | 100% | 21.7 | 130 |
| | NaCl | No | | | |

TABLE 2-continued

| Formulation: 600 µM A22K(Nᵉ(eicosanedioyl-gGlu-OEG-OEG)), B29R, desB30 human insulin 7 mM phosphate pH 7.4 30 mM phenol | Isotonic Agent 174 mM glycerol or 150 mM NaCl | Insulin precipitate | SEC gelfiltration Recovery | SEC gelfiltration Retention time in min | SEC gelfiltration estimation of Mw (kDa) |
|---|---|---|---|---|---|
| 0 Zn/6 insulin, 80 µM HSA | Glycerol | No | 100% | 25/21.7 | 6/130 |
|  | NaCl | No |  |  |  |
| 0 Zn/6 insulin, 60 µM HSA | Glycerol | No | 100% | 25/21.7 | 6/130 |
|  | NaCl | yes |  |  |  |
| 0 Zn/6 insulin, 30 µM HSA | Glycerol | No | 30% | Nd | Nd |
|  | NaCl | Yes |  |  |  |
| 1 Zn/6 insulin | Glycerol | No | Nd | Nd | Nd |
|  | NaCl | Yes |  |  |  |
| 1 Zn/6 insulin, 200 µM HSA | Glycerol | No | Nd | Nd | Nd |
|  | NaCl | No |  |  |  |
| 1 Zn/6 insulin, 120 µM HSA | Glycerol | No | 100% | 21.4 | 130 |
|  | NaCl | No |  |  |  |
| 1 Zn/6 insulin, 80 µM HSA | Glycerol | No | 100% | 25/18.2 | 6/550 |
|  | NaCl | No |  |  |  |
| 1 Zn/6 insulin, 60 µM HSA | Glycerol | No | 100% | 25/17.8 | 6/669 |
|  | NaCl | yes |  |  |  |
| 1 Zn/6 insulin, 30 µM HSA | Glycerol | No | Nd | Nd | Nd |
|  | NaCl | Yes |  |  |  |
| 4 Zn/6 insulin | Glycerol | No | Nd | Nd | Nd |
|  | NaCl | Yes |  |  |  |
| 4 Zn/6 insulin, 200 µM HSA | Glycerol | No | Nd | Nd | Nd |
|  | NaCl | No |  |  |  |
| 4 Zn/6 insulin, 120 µM HSA | Glycerol | No | 100% | 19.4 | 440 |
|  | NaCl | No |  |  |  |
| 4 Zn/6 insulin, 80 µM HSA | Glycerol | No | 100% | 18.2 | 550 |
|  | NaCl | No |  |  |  |
| 4 Zn/6 insulin, 60 µM HSA | Glycerol | No | 100% | 17.5 | 669 |
|  | NaCl | yes |  |  |  |
| 4 Zn/6 insulin, 30 µM HSA | Glycerol | No | Nd | Nd | Nd |
|  | NaCl | Yes |  |  |  |
| 6 Zn/6 insulin | Glycerol | No | Nd | Nd | Nd |
|  | NaCl | Yes |  |  |  |
| 6 Zn/6 insulin, 200 µM HSA | Glycerol | No | Nd | Nd | Nd |
|  | NaCl | No |  |  |  |
| 6 Zn/6 insulin, 120 µM HSA | Glycerol | No | Nd | Nd | Nd |
|  | NaCl | No |  |  |  |
| 6 Zn/6 insulin, 80 µM HSA | Glycerol | No | 100% | 19.2 | 440 |
|  | NaCl | No |  |  |  |
| 6 Zn/6 insulin, 60 µM HSA | Glycerol | No | 100% | 18.8 | 500 |
|  | NaCl | No |  |  |  |
| 6 Zn/6 insulin, 30 µM HSA | Glycerol | No | Nd | Nd | Nd |
|  | NaCl | Yes |  |  |  |

The conclusion from the above investigation is as follows:

The solubililty of A22K(Nᵉ(eicosanedioyl-γGlu-OEG-OEG)), B29R, desB30 human insulin was investigated in isotonic sodium chloride (150 mM) as a function of zinc and albumin concentration. In the absence of albumin, A22K(Nᵉ(eicosanedioyl-γGlu-OEG-OEG)), B29R, desB30 human insulin forms a precipitate. In the presence of albumin minimum in the stoichiometric amount 7.5 moles of acylated insulins to 1 mole of albumin, the acylated insulin is soluble in the zinc concentration range 0-6 zinc atoms/6 insulins.

In native gelfiltration, where the mobile phase is 10 mM Tris, 140 mM NaCl, the recovery of A22K(Nᵉ(eicosanedioyl-γGlu-OEG-OEG)), B29R, desB30 human insulin was investigated for formulations with glycerol as isotonic agent as a function of zinc and albumin concentration. In the absence of albumin the recovery of acylated insulin was reduced indicating precipitation of insulin in the mobile phase. In the presence of albumin the recovery of the acylated insulin corresponded to 100%. The retention time of the acylated insulin mixed with albumin was decreased with decreasing albumin concentration. For formulations with no zinc, the albumin-acylated insulin complex was measured to consist of two albumin molecules oligomerised by an acylated insulin dimer. For formulations with 1 zinc ion per insulin hexamer, the insulin-albumin complex was measured to the size of two albumin molecules oligomerised by an acylated insulin dimer at the ratio 5 insulin molecules per albumin molecule. For the ratios 7.5 and 10 insulin molecules per albumin molecule, two peaks were detected, one corresponds to monomeric insulin and one corresponding to the size of several acylated insulin hexamers binding several albumin molecules.

For formulations with 3, 4 and 6 zinc ions per insulin molecule, large oligomers were formed corresponding to the size of several acylated insulin hexamers binding several albumin molecules.

It is concluded that, in the minimum ratio 7.5 insulin molecule per albumin molecules, albumin keeps the acylated insulin soluble, both in a formulation with 150 mM NaCl and also in native gel-filtration.

Furthermore, it is shown that the acylated insulin dimer forms a complex with two albumin molecules. In the presence of 1 Zn ion per 6 insulin molecules and albumin, a fraction of the acylated insulin in hexamers is bound to albumin and a fraction of the acylated insulin is on the monomeric form bound to albumin. In the presence of 3, 4 or 6 zinc ions per 6 insulin molecules, no monomeric insulin is detected and large insulin hexamer-albumin oligomers are formed.

EXAMPLE 4

A22K(N$^\epsilon$(eicosanedioyl-γGlu-OEG-OEG)), B29R, desB30 human insulin is dissolved in Milli-Q yielding samples according to table 3 containing 7 mM Tris pH 7.4; 1.6% glycerol; 30 mM phenol; 3 Zn per 6 insulin molecules; 1 human serum albumin per 4 insulin molecules; 150 mM NaCl. The test solution is filtered through a 0.2 μm filter and the resulting insulin concentration in the supernatant was measured by standard reverse phase HPLC using human insulin as reference.

Resulting amount of soluble insulin is reported in table 3.

TABLE 3

| Insulin concentration before filtration | Amount of insulin in solution after filtration, in percentage |
|---|---|
| 300 μM | 100 |
| 600 μM | 100 |
| 1200 μM | 100 |
| 1800 μM | 100 |

The conclusion from the above experiment is that addition of albumin in stoikiometric amounts of 1 albumin molecule per 4 insulin molecules in 150 mM NaCl results in soluble insulin molecule in the concentrations 300 μM, 600 μM, 1200 μM and 1800 μM.

EXAMPLE 5

Figure 3:
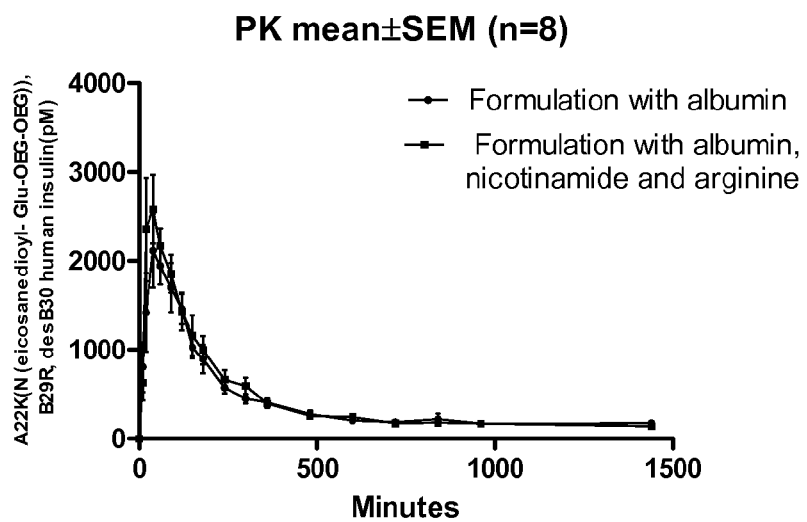
FIG. 3 is a graph showing the measured blood insulin concentration from time 0 to 1500 minutes after injection.
Figure 4:
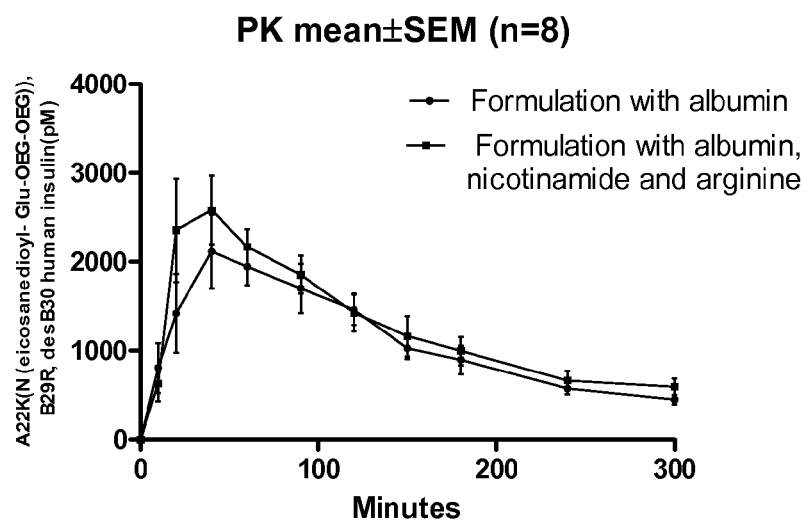
FIG. 4 is a graph illustrating measured blood insulin concentration the first 300 minutes after injection.

Pigs were given equal amounts of A22K(N$^\epsilon$(eicosanedioyl-γGlu-OEG-OEG)), B29R, desB30 human insulin, by subcutaneous administration. The concentration of insulin in the blood was measured after injection and the result is shown in FIGS. 3 and 4. The graph in FIG. 3 shows the result from time 0 to 1500 minutes after injection and the graph in FIG. 4 illustrates the first 300 minutes after injection. In the figures, the following abbreviations are used: "ins" is insulin, "PK" is pharmacokinetic, and "SEM" is standard error mean value. The following formulations were investigated:

1a): 600 uM A22K(N$^\epsilon$(eicosanedioyl-γGlu-OEG-OEG)), B29R, desB30 human insulin, 150 μM pig serum albumin, 3 Zn/hexamer insulin, 1 Zn/pig serum albumin, 174 mM glycerol, 30 mM phenol, pH 7.4.

1b): 600 uM A22K(N$^\epsilon$(eicosanedioyl-γGlu-OEG-OEG)), B29R, desB30 human insulin, 150 μM pig serum albumin, 3 Zn/hexamer insulin, 1 Zn/pig serum albumin, 30 mM arginine, 120 mM nicotinamide, 30 mM phenol, pH 7.4.

The conclusion from the above experiment is that the addition of nicotinamide further increases the bioavailability of the acylated insulin.

EXAMPLE 6

Figure 5:
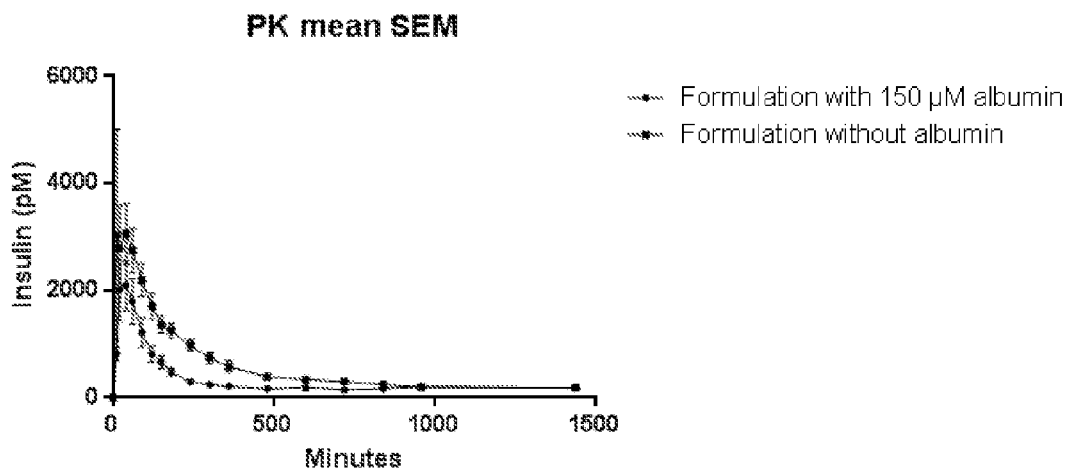
FIG. 5 is a graph showing measured blood insulin concentration from time 0 to 1500 minutes after injection.
Figure 6:
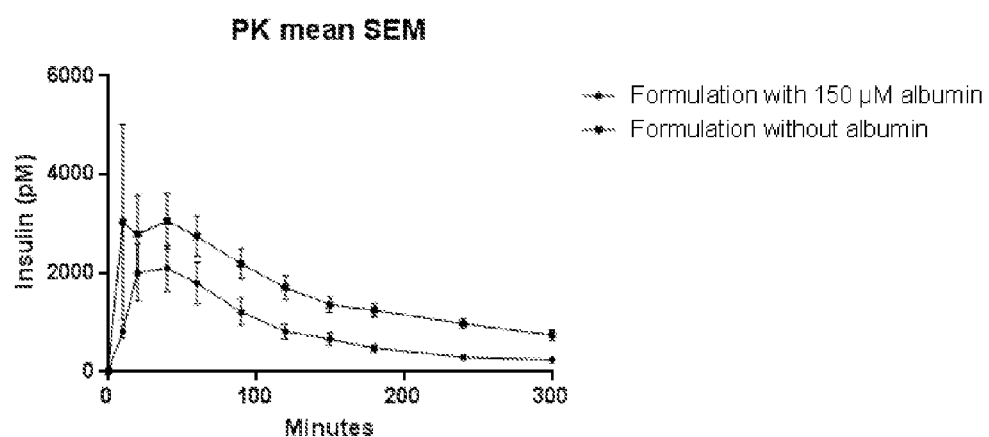
FIG. 6 is a graph illustrating measured blood insulin concentration the first 300 minutes after injection.

Pigs were given equal amounts of A22K(N$^\epsilon$(eicosanedioyl-γGlu-OEG-OEG)), B29R, desB30 human insulin by subcutaneous administration. The concentration of insulin in the blood was measured after injection and the result is shown in FIGS. 5 and 6. The graph in FIG. 5 shows the result from time 0 to 1500 minutes after injection and the graph in FIG. 6 illustrates the first 300 minutes after injection. In the figures, the following abbreviations are used: "ins" is insulin, "PK" is pharmacokinetic, and "SEM" is standard error mean value. The following formulations were investigated:

1a): 600 μM A22K(N$^\epsilon$(eicosanedioyl-γGlu-OEG-OEG)), B29R, desB30, 150 μM pig serum albumin, 3 Zn/hexamer, 1 Zn/albumin, 174 mM glycerol, 30 mM phenol, pH 7.4.

1b): 600 μM A22K(N$^\epsilon$(eicosanedioyl-γGlu-OEG-OEG)), B29R, desB30, 3 Zn/hexamer, 174 mM glycerol, 30 mM phenol, pH 7.4.

The conclusion from the above experiment is that the addition of albumin increases the bioavailability of the acylated insulin.

EXAMPLE 7

A solution of 45 μl 660 uM of 1) A22K(N$^\epsilon$(eicosanedioyl-γGlu-OEG-OEG-OEG-OEG)), A18L, B29R, desB30 human insulin abbreviated to A22K(N$^\epsilon$(C20-γGlu-OEG-OEG-OEG-OEG)), A18L, B29R, 2) A22K(N$^\epsilon$octadecandioyl-γGlu-OEG-OEG)), A18L, B29R, desB30 human insulin (abbreviated to A18L, A22K, Neps C18-γGlu-OEG-OEG), or 3) A22K(N(eps)eicosanedioyl-γGlu-OEG-OEG), desB29-30 human insulin abbreviated to A22K(N$^\epsilon$(C20-γGlu-OEG-OEG)), desB29-30, in formulation according to Table 4 was mixed with 5 μl of sodium chloride solution in concentration according to Table 4. 48 hours after the two solutions were mixed the amount of precipitated acylated insulin was determined after filtration. The concentration determination was carried out by HPLC measurement of insulin in solution. The percentage amount of soluble acylated insulin in relation to the total amount of acylated insulin present in the test solution must be above 30% at a sodium chloride concentration of 150 mM, preferably above 50% at 150 M sodium chloride and most preferred above 60% at 150 mM.

TABLE 4

| Formulation: 600 μM insulin, 300 μM zinc acetate, 7 mM phosphate pH 7.4, 30 mM phenol | NaCl concentration, in mM | % insulin in solution |
|---|---|---|
| A22K(N$^\epsilon$(C20-γGlu-OEG, OEG, OEG-OEG)), A18L, B29R | 0 | 100 |
| | 5 | |
| | 10 | |
| | 25 | |
| | 50 | 100 |
| | 75 | 100 |
| | 100 | |
| | 125 | 46 |
| | 150 | |
| | 175 | 13 |
| | 200 | 13 |
| A18L, A22K, Neps C18-γGlu-OEG-OEG | 0 | 100 |
| | 5 | |
| | 10 | 100 |
| | 25 | |
| | 50 | 100 |
| | 75 | |
| | 100 | 100 |
| | 125 | 75 |
| | 150 | |
| | 175 | 58 |
| | 200 | 50 |
| A22K(N$^\epsilon$(C20-γGlu-OEG-OEG)), desB29-30 | 0 | |
| | 5 | 100 |
| | 10 | 100 |
| | 15 | 100 |
| | 20 | 100 |
| | 34 | 15 |
| | 62 | 7 |
| | 100 | 3 |

EXAMPLE 8

A solution of 45 µl 660 uM of 1) A22K(N$^\epsilon$octadecandioyl-γGlu-OEG-OEG)), A18L, B29R, desB30 human insulin (abbreviated to A18L, A22K, Neps C18-γGlu-OEG-OEG), or 2) A22K(N(eps)eicosanedioyl-γGlu-OEG-OEG), desB29-30 human insulin abbreviated to A22K(N$^\epsilon$(C20-γGlu-OEG-OEG)), desB29-30, in formulation according to Table 5 was mixed with 5 µl of sodium chloride solution in concentration according to Table 5. 48 hours after the two solutions were mixed the amount of precipitated acylated insulin was determined after filtration. The concentration determination was carried out by HPLC measurement of insulin in solution. The percentage amount of soluble acylated insulin in relation to the total amount of acylated insulin present in the test solution must be above 30% at a sodium chloride concentration of 150 mM, preferably above 50% at 150 M sodium chloride and most preferred above 60% at 150 mM.

TABLE 5

| Formulation: 600 µM insulin, 7 mM phosphate pH 7.4, 30 mM phenol | NaCl concentration, in mM | % insulin in solution |
|---|---|---|
| A18L, A22K, Neps C18-γGlu-OEG-OEG | 0 | 100 |
| | 5 | |
| | 10 | 100 |
| | 25 | |
| | 50 | 100 |
| | 75 | |
| | 100 | 23 |
| | 125 | 20 |
| | 150 | 20 |
| | 175 | 13 |
| | 200 | 7 |
| A22K(N$^\epsilon$(C20-γGlu-OEG-OEG)), desB29-30 | 0 | 100 |
| | 5 | |
| | 10 | 27 |
| | 20 | 27 |
| | 34 | 23 |
| | 50 | 13 |
| | 62 | 3 |
| | 100 | 3 |

Test A
Test for solubility of an acylated insulin in the presence of zinc.

This test is performed as follows: Four mg of the acylated insulin to be tested is dissolved in Milli-Q water yielding a final concentration of 600 µM containing zinc acetate acetate supplied to a final concentration of three zinc ions per six insulin molecules and phenol to a final concentration of 30 mM. The pH value is adjusted to 7.4 using 1 N NaOH. Sodium chloride is added to a final concentration of 150 mM. The test solution is mixed by gentle rotation and incubated one hour at room temperature. The test solution is filtrated through a 0.2 µm filter and the insulin concentration in the filtrate is measured by standard reverse phase HPLC using human insulin as reference.

If the insulin concentration is below 30% of the starting concentration after centrifugation, this acylated insulin is among those covered by the present invention, when mixed with albumin.

Test B
Test for the molecular weight of an insulin-albumin-oligomer

This test is performed as follows: Four mg of the acylated insulin to be tested is dissolved in Milli-Q yielding a final concentration of 600 µM containing zinc acetate acetate supplied to a final concentration of three zinc ions per six insulin molecules. Human serum albumin is added to a final concentration of 150 µM and phenol to a final concentration of 30 mM. The pH value is adjusted to 7.4 using 1 N NaOH. The test solution is applied to a gelfiltration column equilibrated in Tris pH 7.4, 140 mM NaCl and the molecular weight of the oligomers in the test solution is measured using the molecular weight standards and the gelfiltration method described by Jonassen, I., Havelund, S., Ribel, U., Plum, A., Loftager, M., Hoeg-Jensen, T., Vølund, A., and Markussen, J. in: *Pharmaceutical Research*, 2006; 23, 1; 49-55.

Acylated insulins forming aggregates of 440 kDa or higher in the described test solution are covered by the present invention, when mixed with albumin.

Test C
Test for solubility of an acylated insulin in the absence of zinc.

This test is performed as follows: Four mg of the acylated insulin to be tested is dissolved in Milli-Q yielding a final concentration of 600 µM containing phenol to a final concentration of 30 mM, The pH value is adjusted to 7.4 using 1 N NaOH. Sodium chloride is added to a final concentration of 150 mM. The test solution is mixed by gentle rotation and incubated one hour at room temperature. The test solution is filtrated through a 0.2 µm filter and the insulin concentration in the filtrate is measured by standard reverse phase HPLC using human insulin as reference. If the insulin concentration is below 50% of the starting concentration after centrifugation, this acylated insulin is among those covered by the present invention, when mixed with albumin.

What claimed is:

1. A pharmaceutical formulation comprising: an acylated insulin and albumin wherein at least 99% (weight/weight) of the acylated insulin is dissolved and wherein not more than 1% (weight/weight) of the acylated insulin is covalently bound to albumin, wherein the acylated insulin is a salting out, acylated insulin; and wherein the molar ratio between albumin and acylated insulin is in the range from about 1:3 to about 1:10; and wherein the formulation is for use by injection.

2. A pharmaceutical formulation comprising a salting out acylated insulin and albumin wherein all of the salting out acylated insulin is dissolved and wherein there is no covalent bond between the salting out acylated insulin and albumin, wherein the formulation is for use by injection.

3. A pharmaceutical formulation according to claim 1, wherein the salting out, acylated insulin is an acylated insulin which has a solubility in a 150 mM NaCl solution, of below 30%.

4. A pharmaceutical formulation according to claim 1, wherein the salting out, acylated insulin is an acylated insulin which forms an insulin-albumin-oligomer with a molecular weight above 440,000.

5. A pharmaceutical formulation according to claim 1, wherein the formulation is selected from the following:
   a): 300 uM A22K(N$^\epsilon$(eicosanedioyl-γGlu-OEG-OEG)), B29R, desB30 human insulin, 7 mM phosphate, pH 7.4, 300 µM pig serum albumin, 150 mM NaCl, 0 Zn/hexamer insulin,
   b): 600 uM A22K(N$^\epsilon$(eicosanedioyl-γGlu-OEG-OEG)), B29R, desB30 human insulin, 7 mM phosphate, pH 7.4, 174 mM glycerol, 30 mM phenol, 3 Zn/hexamer insulin,
   c): 600 uM A22K(N$^\epsilon$(eicosanedioyl-γGlu-OEG-OEG)), B29R, desB30 human insulin, 7 mM phosphate, pH 7.4, 174 mM glycerol, 0 Zn/6 insulin molecules, and
   d): 600 uM A22K A22K(N$^\epsilon$(eicosanedioyl-γGlu-OEG-OEG)), B29R, desB30 human insulin, 7 mM phosphate, pH 7.4, 150 mM NaCl, 0 Zn/6 insulin molecules.

6. A pharmaceutical formulation according to claim 2, wherein the salting out, acylated insulin is an acylated insulin which has a solubility in a 150 mM NaCl solution, of below 30%.

7. A pharmaceutical formulation according to claim 2, wherein the salting out, acylated insulin is an acylated insulin which forms an insulin-albumin-oligomer with a molecular weight above 440,000.

8. A pharmaceutical formulation according to claim 2, wherein the formulation is selected from the following:
- a): 300 uM A22K($N^\epsilon$(eicosanedioyl-γGlu-OEG-OEG)), B29R, desB30 human insulin, 7 mM phosphate, pH 7.4, 300 μM pig serum albumin, 150 mM NaCl, 0 Zn/hexamer insulin,
- b): 600 uM A22K($N^\epsilon$(eicosanedioyl-γGlu-OEG-OEG)), B29R, desB30 human insulin, 7 mM phosphate, pH 7.4, 174 mM glycerol, 30 mM phenol, 3 Zn/hexamer insulin,
- c): 600 uM A22K($N^\epsilon$(eicosanedioyl-γGlu-OEG-OEG)), B29R, desB30 human insulin, 7 mM phosphate, pH 7.4, 174 mM glycerol, 0 Zn/6 insulin molecules, and
- d): 600 uM A22K A22K($N^\epsilon$(eicosanedioyl-γGlu-OEG-OEG)), B29R, desB30 human insulin, 7 mM phosphate, pH 7.4, 150 mM NaCl, 0 Zn/6 insulin molecules.

9. A formulation, according to claim 1, wherein the molar ratio between albumin and acylated insulin is in the range of about 1:5.

10. A formulation, according to claim 1, wherein the molar ratio between albumin and acylated insulin is in the range of about 1:7.

11. A formulation according to claim 1, wherein at least 99.9% (weight/weight) of the acylated insulin is dissolved.

* * * * *